United States Patent
Matsuda et al.

(10) Patent No.: US 6,759,557 B2
(45) Date of Patent: Jul. 6, 2004

(54) MELANIN PRODUCTION INHIBITORS AND SKINCARE PRODUCTS CONTAINING SUCH INHIBITORS

(75) Inventors: Hiroyuki Matsuda, Hiratsuka (JP); Hiroyasu Kumamoto, Hiratsuka (JP); Eiko Tamai, Hiratsuka (JP); Misao Yagi, Hiratsuka (JP); Kenichi Yamamoto, Hiratsuka (JP); Toshimitsu Hagiwara, Hiratsuka (JP); Shinya Watanabe, Hiratsuka (JP)

(73) Assignee: Takasago International Corporation, Tokyo (JP)

(*) Notice: Subject to any disclaimer, the term of this patent is extended or adjusted under 35 U.S.C. 154(b) by 0 days.

(21) Appl. No.: 10/164,702

(22) Filed: Jun. 10, 2002

(65) Prior Publication Data

US 2003/0049213 A1 Mar. 13, 2003

(30) Foreign Application Priority Data

Jun. 8, 2001 (JP) .................................. 2001-173655
Oct. 12, 2001 (JP) .................................. 2001-315378

(51) Int. Cl.$^7$ ...................... C07C 49/105; C07C 35/20; A01N 35/00
(52) U.S. Cl. ...................... 568/375; 568/377; 568/821; 568/823; 514/690
(58) Field of Search ................................ 568/376, 377, 568/821, 823

(56) References Cited

U.S. PATENT DOCUMENTS

| 5,731,303 A | 3/1998 | Hsieh ........................ 514/183 |
| 6,057,372 A | 5/2000 | Nobuhiro et al. ........... 514/675 |
| 6,087,322 A | 7/2000 | Morelli et al. ................ 512/25 |
| 6,200,254 B1 | 3/2001 | Lupo, Jr. et al. ................ 572/8 |

FOREIGN PATENT DOCUMENTS

| JP | 9-151129 A | 6/1997 |
| JP | 3087921 B2 | 7/2000 |

OTHER PUBLICATIONS

Harrison, I.T., et al.; "The Synthesis of a Stable Complex of a Macrocycle and a Threaded Chain"; *Journal of the American Chemical Society*; vol. 89, No. 22, pp. 5723–5724; Oct. 25, 1967.
Schill, G., et al.; "Statistische Synthesen von Rotaxanen"; *Chem. Ber.*; vol. 113, pp. 941–954; 1980.
Ashkenazi, P., et al.; "Preparation and Labelling of [20.3.3] Propellane–24, 27–dione"; *Helvetica Chimica Acta*; vol.68, pp. 2033–2035; 1985.
Russell, G.A., et al.; "Conformational Studies of Macrocyclic 1, 2–Semidiones"; *Journal of the American Chemical Society*; vol. 107, pp. 1717–1720; 1985.
Natrajan, A., et al.; "Micellar Control of Organic Reactions: Propellane Substrates as Stereochemical Probes for Micellar Binding"; *Journal of the American Chemical Society*; vol. 109, pp. 7477–7483; 1987.
Prelog, V., et al., "Zur Kenntnis des Kohlenstoffringes. Ein Herstellungsverfahren für vielgliedrige Cyclanone"; *Helvetica Chimica Acta*; vol. 30, No. 6, pp. 1741–1749; Oct. 15, 1947.
Kobelt M., et al.; "Zur Kenntnis des Kohlenstoffringes. Vielgliedrige Cyclanole und Cyclanol–acetate"; *Helvetica Chimica Acta*; vol.32, Mo. 1, pp. 256–265; Feb. 1, 1949.

*Primary Examiner*—James O. Wilson
*Assistant Examiner*—Sikarl A. Witherspoon
(74) *Attorney, Agent, or Firm*—Kubovcik & Kubovcik

(57) ABSTRACT

A melanin synthesis inhibitor composition containing at least one macrocyclic compound represented by Formula (1)

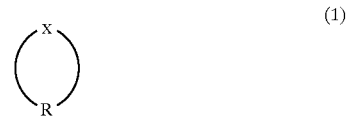

wherein X is a group selected among the groups consisting of C=O; CH—OH and O=C—CHOH; R being a chain hydrocarbon having 13 to 24 carbon atoms, R forms a ring with X and may be saturated or contain 1 to 3 unsaturated bonds and may be substituted by a lower alkyl group of 1 to 3 carbon atoms.

17 Claims, No Drawings

MELANIN PRODUCTION INHIBITORS AND SKINCARE PRODUCTS CONTAINING SUCH INHIBITORS

BACKGROUND OF THE INVENTION

1. Field of the Invention

The present invention relates to new macrocyclic ketone, hydroxy and hydroxyketone compounds and to melanin synthesis inhibitors containing such compounds. The present invention also relates to an external skincare agent containing one or at least two kinds of such melanin synthesis inhibitors.

2. Description of Background Information

Ultra violet rays and other forms of irradiation cause tanning. The colour change (tanning) of the skin tissue has its origin in melanin synthesis and the stagnation of the melanin inside the pigmented cells under the influence of hormones and stimulation by ultraviolet exposure. Freckles, wrinkles and the like are formed by the stagnation and the fixation of melanin inside the surface layer of the skin at some places.

As regards melanin synthesis on the skin surface, tyrosinase, which is an oxidative enzyme synthesised in the pigmented cells, oxidizes and polymerises tyrosine thus synthesising melanin.

There is much research into ways of inhibiting melanin synthesis and its fixation process in order to create a cosmetic whitening agent.

Until now, vitamin C, cysteine, kojic acid, arbutin, glutathione, hydroquinone and other efficient compounds extracted from natural substances are known for inhibiting melanin synthesis by lowering the tyrosinase activity or by bleaching and lightening the colour of the synthesised melanin. However, the stability, safety and whitening effect of these compounds are not sufficient, and no satisfactory whitening agent has been obtained until now.

Moreover, until now, 2-hydroxycyclopentadecanone, which is an intermediate compound in the synthesis of musk fragrance, and which has a macrocyclic hydroxyketone structure comprising a 15 carbon atom ring, is known to be an inhibitor of melanin synthesis having a macrocyclic hydroxyketone structure (JP-A-Hei-9-151129). However, the melanin synthesis inhibiting action of this compound is not sufficient and the development of inhibitors of melanin synthesis having a high activity is still desired.

In U.S. Pat. No. 6,200,254, α-hydroxyketones are disclosed as intermediate compounds in the synthesis of macrocyclic dieneketone compounds of the following chemical Formula (4a)

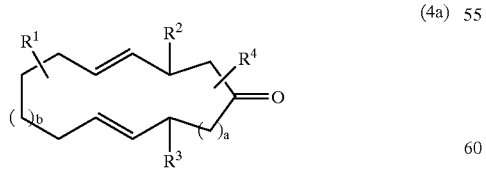

(4a)

(wherein $R^1$, $R^2$, $R^3$ and $R^4$ are hydrogen atom or an alkyl group of 1 to 4 carbon atoms, respectively, "a" being equal to 1 or 2, and "b" being equal to any one of 1 to 6) and the saturated or monounsaturated macrocyclic ketone compounds of Formula (4b)

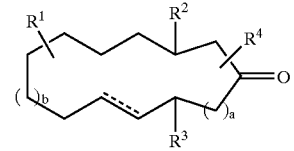

(4b)

(wherein $R^1$, $R^2$, $R^3$ and $R^4$ are hydrogen atom or an alkyl group of 1 to 4 carbon atoms, respectively, "a" being equal to 1 or 2 and b being equal to any one of 1 to 6).

Further, macrohydroxyketones comprising a ring of more carbon atoms, for example 2-hydroxycyclodocosanone which comprises a 22 carbon atom ring and 2-hydroxycyclotetracosanone which comprises a 24 carbon atom ring are known as intermediate compounds in the synthesis of [20.3.3]propelan-24,27-dione and [22.3.3] propelan-26,29-dione respectively (see Helv. Chim. Acta, 68, 2033 (1985), J. Am. Chem. Soc., 109, 7477(1987)).

Moreover, 2-hydroxycyclotetracosanone which comprises a 24 carbon atom ring is known as a precursor of trans-tetracosan-1, 2-semidione used in configuration analysis (J. Am. Chem. Soc., 107, 1717(1985)). 2-hydroxycyclohexacosanone comprising a 26 carbon atom ring is known as a compound synthesised via acyloin cyclization reaction of diethyl 1,26-hexacosanedioate (Ann. Chim. (Rome), 60(2), 155(1970)).

Further, 2-hydroxycyclooctacosanone which comprises a 28 carbon atom ring and 2-hydroxycyclotriacontanone which comprises a 30 carbon atom ring are reported as used in the construction of a part of the macrocyclic ring of shuttle molecules. (Chem. Ber., 113, 941, 1980; J. Am. Chem. Soc., 89, 5723, 1967).

However, as to macrocyclic compounds comprising a ring of 13 to 19 carbon atoms and of more than 22 carbon atoms, there is no mention of the specificity of α-hydroxyketone groups. Consequently, the macrocyclic α-hydroxyketone compounds comprising a ring of 16 to 26 carbon atoms, were not at all expected to have any activity as melanin synthesis inhibitor.

SUMMARY OF THE INVENTION

An object of the invention is to provide on the one hand an inhibitor of melanin synthesis which has excellent safety and stability, and which has a high inhibiting action on melanin synthesis, and on the other hand an external skincare product containing such an inhibitor.

To this end, there is provided a melanin-synthesis inhibitor composition containing at least one macrocyclic compound represented by Formula (1)

(1)

wherein X signifies a group selected among the groups consisting of —CO—, —CHOH— and —CO—CHOH—; R signifies a chain hydrocarbon having 13 to 24 carbon atoms and forming a ring with X; and R either is saturated or contains 1 to 3 unsaturated bonds, and may be substituted with a lower alkyl group of 1 to 3 carbon atoms, with the proviso that, when X is —CO—CHOH—, the number of carbon atoms in said chain hydrocarbon is not 13; and, optionally, an appropriate ingredient and/or medium.

Typically, in the melanin-synthesis inhibitor compositions of the invention, X signifies a —CO— group.

Such compositions may contain at least one compound selected from the group consisting of cyclotetradecanone, cyclopentadecanone, cyclohexadecanone, cycloheptadecanone, cyclooctadecanone, cyclononadecanone, cycloeicosanone, cycloheneicosanone, cyclodocosanone, cyclotricosanone, cyclotetracosanone, cyclopentacosanone, 3-methylcyclopentadecanone, (S)-3-methylcyclopentadecanone, (R)-3-methylcyclopentadecanone, 3-methylcyclohexadecanone, 4-methylcyclohexadecanone, 4-cyclopentadecenone, 5-cyclopentadecenone, 4-cyclohexadecenone, 5-cyclohexadecenone, (E)-5-cyclohexadecenone, (Z)-5-cyclohexadecenone, 9-cyclopentadecenone, (E)-9-cyclopentadecenone, (Z)-9-cyclopentadecenone, 3-methyl-4-cyclopentadecenone, 3-methyl-5-cyclopentadecenone, 3-methyl-4-cyclohexadecenone, 3-methyl-5-cyclohexadecenone, 4-methyl-4-cyclohexadecenone, 4-methyl-5-cyclohexadecenone, 10-cycloeicosenone, 11-cyclodocosenone and 12-cyclotetracosenone.

Alternatively, in the melanin-synthesis inhibitor compositions of the invention, X signifies a —CHOH— group.

Such compositions may contain at least one compound selected from the group consisting of cyclotetradecanol, cyclopentadecanol, cyclohexadecanol, cycloheptadecanol, cyclooctadecanol, cyclononadecanol, cycloeicosanol, cycloheneicosanol, cyclodocosanol, cyclotricosanol, cyclotetracosanol, cyclopentacosanol, 3-methylcyclopentadecanol, (1R, 3R)-3-methylcyclopentadecanol, (1R, 3S)-3-methylcyclopentadecanol, (1s, 3R)-3-methylcyclopentadecanol, (1s, 3S)-3-methylcyclopentadecanol, 3-methylcyclohexadecanol, (4-methylcyclohexadecanol, 4-cyclopentadecenol, 5-cyclopentadecenol, 4-cyclohexadecenol, 5-cyclohexadecenol, (E)-5-cyclohexadecenol, (S)-5-cyclohexadecenol, 9-cycloheptadecenol, (E)-9-cycloheptadecenol, (S)-9-cycloheptadecenol, 3-methyl-4-cyclopentadecenol, 3-methyl-5-cyclohexadecenol, 4-methyl-4-cyclohexadecenol, 4-methyl-5-cyclohexadecenol, 10-cycloeicosenol, 11-cyclodocosenol and 12-cyclotetracosenol.

Preferably, the melanin synthesis inhibitor compositions contain at least one macrocyclic compound of Formula (1) where X signifies group —CO—, and at least one macrocyclic compound of Formula (1) where X signifies group —CHOH—.

Alternatively yet, in the melanin synthesis inhibitor compositions of the invention, X signifies a —CO—CHOH— group, R being a chain hydrocarbon having 14 to 24 carbon atoms.

Such compositions may contain at least one compound selected from the group consisting of 2-hydroxycyclohexadecanone, 2-hydroxycycloheptadecanone, 2-hydroxycyclooctadecanone, 2-hydroxycyclononadecanone, 2-hydroxycycloeicosanone, 2-hydroxycycloheneicosanone, 2-hydroxycyclodocosanone, 2-hydroxycyclotricosanone, 2-hydroxycyclotetracosanone, 2-hydroxycycloheptacosanone, 2-hydroxycyclohexacosanone, 2-hydroxycyclo-3-methylcycloeicosanone, 2-hydroxy-20-methylcycloeicosanone, 2-hydroxy-4,19-dimethylcycloeicosanone, (4R)-2-hydroxy-4-methylcycloeicosanone, (19R)-2-hydroxy-19-methylcycloeicosanone, 2-hydroxy-8-cyclohexadecenone, 2-hydroxy-9-cycloheptadecenone, 2-hydroxy-10-cyclooctadecenone, 2-hydroxy-10-cyclononadecenone, 2-hydroxy-11-cycloeicosenone, (Z)-2-hydroxy-11-cycloeicosenone, (E)-2-hydroxy-11-cycloeicosenone, 2-hydroxy-10-cycloheneicosenone, 2-hydroxy-11-cyclodocosenone, 2-hydroxy-13-cyclotetracosenone, 2-hydroxy-3-methyl-11-cycloeicosenone, 2-hydroxy-20-methyl-11-cycloeicosenone, 2-hydroxy-4,19-dimethyl-11-cycloeicosenone, (4S)-2-hydroxy-4-methyl-11-cycloeicosenone, (19S)-2-hydroxy-19-methyl-11-cycloeicosenone, (5E, 15E)-2-hydroxy-5,15-cyclooctadecadienone, (5E, 17E)-2-hydroxy-4,19-dimethyl-5,17-cycloeicosadienone, Preferably, R is a chain hydrocarbon having 16 to 22 carbon atoms.

Preferably yet, R is a chain hydrocarbon having 18 or 19 carbon atoms.

Such compositions may contain at least one compound selected from the group consisting of 2-hydroxycycloeicosanone, 2-hydroxycycloheneicosanone, 2-hydroxy-11-cycloeicosenone, 2-hydroxy-11-cycloheneicosenone and 2-hydroxy-12-cycloheneicosenone.

The invention also relates to an external skincare product, characterised in that it contains at least one composition as defined above.

Preferably, the skincare product contains at least one composition defined above in a concentration ranging from 0.00001 to 10 weight %.

The invention further relates to a macrocyclic compound represented by Formula (1):

wherein X signifies a —CO—CHOH— group; R signifies a chain hydrocarbon having 18 or 19 carbon atoms and forming a ring with X; and R either is saturated or contains 1 to 3 unsaturated bonds, and may be substituted with a lower alkyl group of 1 to 3 carbon atoms.

Such a macrocyclic compound may be selected from the group consisting of 2-hydroxycycloeicosanone, 2-hydroxycycloheneicosanone, 2-hydroxy-11-cycloeicosenone, 2-hydroxy-11-cycloheneicosenone and 2-hydroxy-12-cycloheneicosenone.

Typically, the above macrocyclic compound is prepared by a method comprising the steps of:
 preparing a corresponding unsaturated chain hydrocarbon having 20 or 21 carbon atoms, whose both end carbons form esterified carboxy groups;
 subjecting said esters to an acyloin condensation, so that an unsaturated macrocyclic compound is obtained; and optionally,
 subjecting said unsaturated macrocyclic compound to subsequent hydrogenation.

The invention further concerns a process of inhibiting a melanin synthesis using a compound of Formula (1) defined above.

Methyl, ethyl, n-propyl and isopropyl groups may be given as examples of lower alkyl group having 1 to 3 carbon atoms.

The invention will be explained in more detail on the basis of the following examples of synthesis of compounds according to the invention and of results regarding the melanin synthesis inhibiting effect of the compounds of the present invention.

The above, and other objects, features and advantages of the invention will be made apparent from the following description of the preferred embodiments, given as non-limiting examples.

DETAILED DESCRIPTION OF THE PREFERRED EMBODIMENTS

As mentioned above, preferred examples of melanin-synthesis inhibitor compounds, in which X is —CO—, include: cyclotetradecanone, cyclopentadecanone, cyclohexadecanone, cycloheptadecanone, cyclooctadecanone, cyclononadecanone, cycloeicosanone, cycloheneicosanone, cyclodocosanone, cyclotricosanone, cyclotetracosanone, cyclopentacosanone, 3-methylcyclopentadecanone, (S)-3-methylcyclopentadecanone, (R)-3-methylcyclopentadecanone, 3-methylcyclohexadecanone, 4-methylcyclohexadecanone, 4-cyclopentadecenone, 5-cyclopentadecenone, 4-cyclohexadecenone, 5-cyclohexadecenone, (E)-5-cyclohexadecenone, (Z)-5-cyclohexadecenone, 9-cyclopentadecenone, (E)-9-cyclopentadecenone, (Z)-9-cyclopentadecenone, 3-methyl-4-cyclopentadecenone, 3-methyl-5-cyclopentadecenone, 3-methyl-4-cyclohexadecenone, 3-methyl-5-cyclohexadecenone, 4-methyl-4-cyclohexadecenone, 4-methyl-5-cyclohexadecenone, 10-cycloeicosenone, 11-cyclodocosenone, 12-cyclotetracosenone and the like.

However, the invention is not limited to the above compounds.

Likewise, as mentioned above, preferred examples of melanin-synthesis inhibitor compounds, in which X is —CHOH—, include: cyclotetradecanol, cyclopentadecanol, cyclohexadecanol, cycloheptadecanol, cyclooctadecanol, cyclononadecanol, cycloeicosanol, cycloheneicosanol, cyclodocosanol, cyclotricosanol, cyclotetracosanol, cyclopentacosanol, 3-methylcyclopentadecanol, (1R,3R)-3-methylcyclopentadecanol, (1R,3S)-3-methylcyclopentadecanol, (1S,3R)-3-methylcyclopentadecanol, (1S,3S)-3-methylcyclopentadecanol, 3-methylcyclohexadecanol, 4-methylcyclohexadecanol, 4-cyclopentadecenol, 5-cyclopentadecenol, 4-cyclohexadecenol, 5-cyclohexadecenol, (E)-5-cyclohexadecenol, (S)-5-cyclohexadecenol, 9-cycloheptadecenol, (E)-9-cycloheptadecenol, (S)-9-cycloheptadecenol, 3-methyl-4-cyclopentadecenol, 3-methyl-5-cyclohexadecenol, 4-methyl-4-cyclohexadecenol, 4-methyl-5-cyclohexadecenol, 10-cycloeicosenol, 11-cyclodocosenol, 12-cyclotetracosenol and the like.

However, the invention is not limited to the above compounds.

Among the examples of melanin-synthesis inhibitor compounds described supra, in which X is —CO—CHOH—, examples of saturated compounds include:
2-hydroxycyclohexadecanone, 2-hydroxycycloheptadecanone, 2-hydroxycyclooctadecanone, 2-hydroxycyclononadecanone, 2-hydroxycycloeicosanone, 2-hydroxycycloheneicosanone, 2-hydroxycyclodocosanone, 2-hydroxycyclotricosanone, 2-hydroxycyclotetracosanone, 2-hydroxycycloheptacosanone, 2-hydroxycyclohexacosanone, 2-hydroxycyclo-3-methylcycloeicosanone, 2-hydroxy-20-methylcycloeicosanone, 2-hydroxy-4,19-dimethylcycloeicosanone, (4R)-2-hydroxy-4-methylcycloeicosanone, (19R)-2-hydroxy-19-methylcycloeicosanone.

Likewise, examples of unsaturated compounds include:
2-hydroxy-8-cyclohexadecenone, 2-hydroxy-9-cycloheptadecenone, 2-hydroxy-10-cyclooctadecenone, 2-hydroxy-10-cyclononadecenone, 2-hydroxy-11-cycloeicosenone, (Z)-2-hydroxy-11-cycloeicosenone, (E)-2-hydroxy-11-cycloeicosenone, 2-hydroxy-10-cycloheneicosenone, 2-hydroxy-11-cyclodocosenone, 2-hydroxy-13-cyclotetracosenone, 2-hydroxy-3-methyl-11-cycloeicosenone, 2-hydroxy-20-methyl-11-cycloeicosenone, 2-hydroxy-4,19-dimethyl-11-cycloeicosenone, (4S)-2-hydroxy-4-methyl-11-cycloeicosenone, (19 S)-2-hydroxy-19-methyl-11-cycloeicosenone, (5E,15E)-2-hydroxy-5,15-cyclooctadecadienone, (5E,17E)-2-hydroxy-4,19-dimethyl-5,17-cycloeicosadienone and the like.

However, the compounds of the invention are not limited to the above examples.

Among the chemical compounds of the invention shown in Formula (1), there are isomers which have a different optical activity due to the (R,S) structure of the asymmetric carbon atom existing when the carbon atom has an hydroxyl group and when the chain hydroxyl group is substituted. However, in the present invention, both of the isomers and the racemic mixture thereof can be used. Further, both of the cis and trans isomers formed by the presence of a double bond and the mixture thereof can be used.

Among the melanin inhibitors of the invention shown in Formula (1), the macrocyclic α-hydroxyketone compounds comprising a ring of 20 or 21 carbon atoms and represented by the following Formula (2) are novel compounds unknown until now. These compounds show a melanin synthesis inhibiting effect, and are stable and storable.

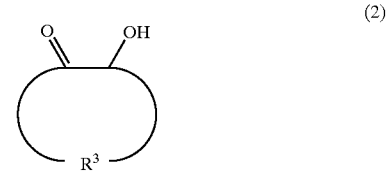

(2)

(wherein $R^3$ which is a part of a 20 or 21 carbon atom ring, is a chain hydrocarbon group containing 18 or 19 carbon atoms; $R^3$ may be saturated or contain 1 to 3 unsaturated bonds, and may be substituted by a lower alkyl group of 1 to 3 carbon atoms).

Among the examples of compounds shown in Formula (2), examples of saturated compounds include:
2-hydroxycycloeicosanone, 2-hydroxycycloheneicosanone and the like.

Likewise, examples of unsaturated compounds include:
2-hydroxy-11-cycloeicosenone, 2-hydroxy-11-cycloheneicosenone, 2-hydroxy-12-cycloheneicosenone and the like.

However, the compounds of the invention shown in Formula (2) are not limited to these examples.

The compounds of Formula (2) can be synthesised, for example, through a known method of acyloin condensation reaction (JP-B-3087921). There is thus provided a chain hydrocarbon with a corresponding number of carbon atoms, both ends of which form carboxy groups. Diesters of such dicarboxylic acid (I) are condensed to give compound (II). Further, when compound (II) is unsaturated, a saturated compound (III) can be obtained easily through a common hydrogenation method:

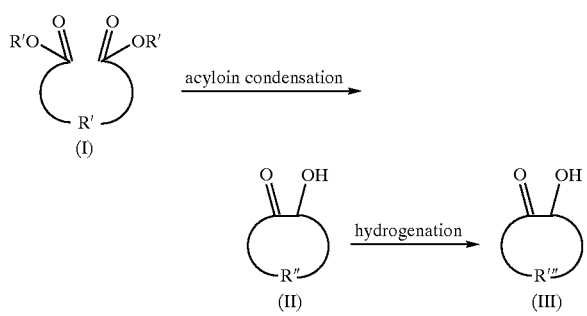

(wherein R' is a lower alkyl group of 1 to 4 carbon atoms; R" of compound (I) or (II) is a chain hydrocarbon group of 14 to 24 carbon atoms, which comprises preferably 1 to 3 unsaturated bonds and may be substituted by a lower alkyl group of 1 to 3 carbon atoms; R" of compound (II) comprises a 14 to 24 carbon atom chain hydrocarbon forming part of a 16 to 26-carbon atom ring, and may be substituted by a lower alkyl group of 1 to 3 carbon atoms; when the chain hydrocarbon group of (II) is saturated, there is no hydrogenation reaction bringing compound (II) to compound (III); R'" is a saturated chain hydrocarbon group comprising 14 to 24 carbon atoms, and forms part of a 16 to 26 carbon atom ring of compound (III); R'" may be substituted by a lower alkyl group of 1 to 3 carbon atoms).

Diesters of dicarboxylic acid (I) comprising an appropriate number of carbon atoms, in which R" typically comprises at least one unsaturated bond, can be obtained, for example, through the metathesis reaction of one or several kinds of unsaturated esters as shown below.

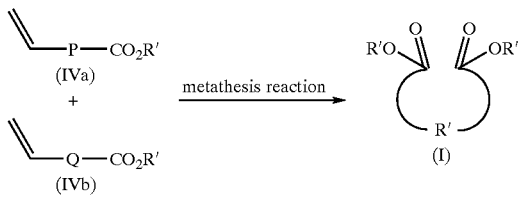

(wherein R' is a lower alkyl group of 1 to 4 carbon atoms, R" is a chain hydrocarbon group of 14 to 24 carbon atoms which typically comprises 1 to 3 unsaturated bonds and may be substituted with a lower alkyl group of 1 to 3 carbon atoms. P and Q are (independently) chain hydrocarbon groups of 2 to 18 carbon atoms, which may be substituted by 1 to 3 lower alkyl groups, respectively. However, the sum of the chain carbon atoms in the chain hydrocarbon groups P and Q is from 10 to 20).

As regards the unsaturated esters (IVa) and (IVb) of the above-mentioned formula, products available on the market (for example, 10-methyl undecenoate (manufactured by Tokyo Kasei)) can be used directly or possibly purified before use. Further, 3-methyl substituted unsaturated esters, which contain optically active forms, can be obtained through the method disclosed in JP-A-2000-53675.

The above-mentioned metathesis reaction between the unsaturated esters (IVa) and (IVb) is possible without any solvent, but any inactive solvent which does not participate to the reaction can be used. They include, for example, organic solvents such as methylene chloride, chloroform and other chlorinated solvents, benzene, chlorobenzene, toluene, xylene and other aromatic type solvents, diethyl ether, diisopropyl ether, tetrahydrofuran, dimethoxyethane, 1,3-dioxolane and other ether-type solvents, and a mixture of these organic solvents. These organic solvents or their mixture can be used in an amount of 1 to 100 times the volume of the unsaturated esters (IVa) and (IVb), in the presence of $\frac{1}{1000}$ to $\frac{1}{5}$ moles of Grubbs catalyst per mole of the above-mentioned esters. The reaction is performed normally at about 5 to about 50° C. and is terminated in about 1 to about 20 hours. After reaction, a further treatment according to a usual method is performed.

The acyloin condensation of the obtained compounds (I) is performed using, for example, benzene, toluene, xylene, naphthalene or other aromatic solvents in a ratio of 5 to 100 times by volume with respect to the compounds (I), in the presence of 4 to 8 moles of sodium, lithium or other alkali metals per mole of compound (I); if necessary, an additive such as trimethylsilyl chloride can be used in an amount of 4 to 8 moles per mole of compound (I). The reaction is usually performed at about 100 to about 150° C., and is terminated in about 1 to about 10 hours. After reaction, a further treatment according a conventional method is performed.

The solvent which can be used for the above-mentioned hydrogenation of the compounds (II) obtained may be any solvent which does not participate in the reaction. They include, for example, organic solvents such as methanol, ethanol, 2-propanol, and other alcohol-type solvents, diethyl ether, diisopropylether, tetrahydrofuran, dimethoxyethane, 1,3-dioxolane, and other ether-type solvents, and hexane, heptane, octane and other hydrocarbon-type solvents. These organic solvents or their mixture can be used in an amount of 1 to 100 times the volume of the compounds (I), in the presence of 0.1 to 50% by weight of palladium carbon, palladium-alumina, palladium-silica, palladium black and other metal-containing catalysts and under a hydrogen pressure of atmospheric pressure to about 6650 Pa. The reaction is performed typically at 0° C. to 100° C. approximately and is terminated after about 1 to about 20 hours. After reaction, a further treatment according a usual method is performed.

Further, as regards $R^1$–$R^3$ in Formulae (I)–(III), diesters of a dicarboxylic acid comprising the required number of carbon atoms and having at least two unsaturated bonds can be synthesised according to, e.g. the method disclosed in U.S. Pat. No. 6,200,254.

Thus, a long chain hydrocarbon comprising dialdehyde at its both ends is first transformed into a diallylalcohol form by double quantity of one or several kinds of vinyl Grignard reagents. The resulting product is then transformed into diester of a corresponding dicarboxylic acid (2') through Claisen rearrangement using trialkylorthoformate.

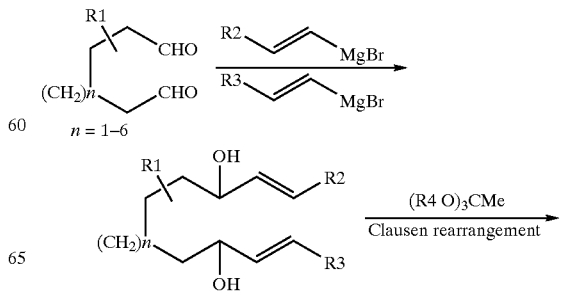

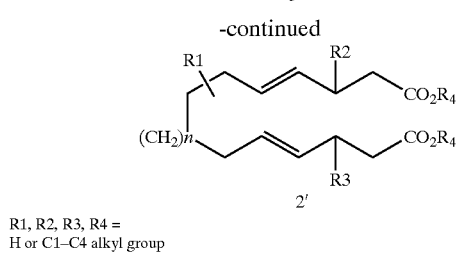

R1, R2, R3, R4 =
H or C1–C4 alkyl group

However, the preparation of the compounds of Formula (1) is not limited to the above method, and any other production method may be used.

The compounds of Formula (1) have a melanin-synthesis inhibiting effect on pigmented cells and an excellent storage stability, as shown in the following Examples.

The melanin-synthesis inhibitor composition of the invention may contain only one compound of Formula (1) or at least two compounds thereof. Moreover, the melanin-synthesis inhibitor composition of the invention may contain one or several kinds of compounds of Formula (1), as well as one or several known whitening agents such as pantetheine-S-sulfonic acid, isoferulic acid, ascorbic acid and its derivatives, arbutin, kojic acid, linoleic acid, ellagic acid, glycyrrhizic acid and licorice extracts.

Further, the melanin-synthesis inhibitor composition of the invention may contain one or at least two compounds of Formula (1), together with an ultra-violet ray absorbent. It is then possible to obtain a melanin-synthesis inhibiting effect and an ultra-violet ray shielding effect. Any known ultra-violet ray absorbent may be used for such purpose. Such ultra-violet ray absorbent includes, for example, dibenzoyl-methane derivatives such as "Parsol 1789", α-dehydroaminoacid derivatives such as "soft shade A" or other UV-A absorbents; esters of p-amino benzoic acid, esters of p-methoxy cinnamic acid, 2-phenylbenzoimidazol derivatives, benzophenone derivatives such as 4-phenylbenzophenone, salicylic acid derivatives such as phenyl salicylate, and UV-B absorbents such as derivatives of gallic acid. One or several kinds of these compounds may be used depending on the circumstances.

The external skincare agent of the invention includes a cosmetic, a drug or a para- or non-medicinal product. The form of the external skincare agent is not limited, and may take any form used for cosmetics, medicines or non- or para-medical products, such as perfume water, milky lotion, packing, foundation, cream, unguent, agents for bath, a gel or the like.

The concentration of the melanin-synthesis inhibitor composition in the formulation of the external skincare agent may vary depending on the type of base material used, on whether it is used with other melanin-synthesis inhibitors, and on the intended use. The concentration typically varies from 0.00001 to 10% by weight, preferably from 0.0001 to 1% by weight with respect to the total weight of the skincare agent.

The base material for the skincare agent may be any publicly known base material. There is no particular limitation as far as it does not react with the compounds of the invention. It may be, for example, a solid, a liquid, an emulsion, a bubbling form, a gel or the like The external skincare agent of the invention may also contain any kind of product usually used in medicines, cosmetics or the like as far as it does not degrade the inhibiting activity of the inventive compounds; for example, an aqueous component, an oily component, a powder component, a surfactant, a humectant, lower alcohols or polyols, thickening agent, colorants, perfume, anti oxidant, pH adjusting agent, chelating agent, preservative, ultraviolet protector, emulsifying agent, anti-inflammatory agent, pharmaceutical agent, skin nutrient, or the like.

When the melanin-synthesis inhibitor composition is mixed into a particular form of external skincare agent, the inhibitor composition may be mixed with other ingredients directly, or after having been dissolved in a perfume composition.

Synthesis Examples

The compounds according to Formula (1), where X is —CO— group or —CHOH— group, can be prepared, e.g. by methods described herebelow, but preparation is not limited to such methods.

Measuring Devices and Measuring Conditions:
  (1) Gas chromatography (measure of conversion rate)
    Device: HP-5890A (manufactured by Hewlett Packard Co. Ltd)
    Column: chemical bonded column OV-1, 25 m×0.25 mm (GL Science Co. Ltd)
    Carrier gas: helium
    Measuring temperature: 100 to 200° C. (heating rate of 10° C./min)
  (2) Infrared spectra (1R);
    Device: IR-810 type (Nippon Bunkô Kogyo Co. Ltd)
    Measuring method: film method;
  (3) Proton nuclear magnetic resonance ($^1$H-NMR)
    Device: AM-400 (400 MHz) (Bruker Co. Ltd)
    Internal reference substance: tetramethylsilane.
  (4) Mass spectra (MS)
    Device: M-80B mass spectrometer (ionisation voltage: 20 eV)
    (Hitachi Seisakusho Co. Ltd)

Synthesis Example 1

Synthesis of 10-cycloeicosenone

In a 500 ml four neck reactor equipped with a thermometer and a refrigerant, 10-undecenoate (25 ml), Grubbs catalyst (0.25 g), and methylene chloride (100 ml) were mixed and stirred at room temperature for 16 hours under a nitrogen flow. The reaction mixture was then put under reduced pressure to remove the solvent. The resultant residue was dissolved in methanol (75 ml) and crystallised at −10° C. for 3 hours. The obtained crystals were filtered and washed with methanol (75 ml) cooled to −10° C. to obtain white crystals, which were then dried by a vacuum pump to give 7.2 g of 10-eicosendionic acid dimethyl ester (dimethyl 10-eicosendioate).

In a 200 ml four neck reactor equipped with a thermometer, a dripping funnel and a refrigerant, Na (0.9 g) and anhydrous toluene (60 ml) were introduced and stirred at 105° C. under nitrogen flow. Dimethyl 10-eicosandioate (3.7 g) and a solution of trimethylsilyl chloride (4.4 g) in anhydrous toluene (60 ml) were added dropwise to the reactor over 15 minutes. The resulting mixture was refluxed for 2 hours under heating and stirring. The reaction mixture was cooled and quenched into methanol (60 ml). To this were added a 5% HCl aqueous solution and ethyl acetate, and the total solution was left to separate into two phases. The organic phase was washed twice with water and then washed with a saturated sodium chloride solution. The solvent was removed under reduced pressure to give 3.4 g of crude product.

The crude product was purified on a silica gel column chromatograph (hexane/ethyl acetate=10/1 v/v) to give 2.4 g of 2-hydroxy-11-cycloeicosenone (yield 77%).

In a 50 ml four neck reactor equipped with a thermometer, a dripping funnel and a refrigerant, zinc powder (2.3 g), 2-hydroxy-11-cycloeicosenone (1.4 g) and toluene (10 ml) were mixed, stirred and heated at 90° C. under nitrogen flow. A 20N sulphuric acid aqueous-solution (2.8 ml) was added thereto dropwise over 2.5 hours and the resulting mixture was stirred under heating for 30 minutes. Toluene and water were added after the reaction and the resulting solution was allowed to stand to separate into two phases. The organic phase was washed twice with water and then washed with a saturated sodium chloride aqueous solution. The solvent was removed under reduced pressure to give 1.4 g of crude product. The crude product was purified on a silica gel column chromatograph (hexane/ethyl acetate=10/1, v/v) to give 1.2 g of 10-cycloeicosenone (yield 92%).

$^1$H-NMR (500 MHz, CDCl$_3$, d) ppm: 1.28 (br.s, 30H), 1.57–1.64 (m, 4H), 2.4 0 (t, J=7.0 Hz, 4H).

IR (film) cm$^{-1}$: 3025, 1715.

MS (m/e): 292 (M$^+$), 274, 237, 196, 143, 135, 121, 109, 95, 81, 67, 55, 41, 29

Synthesis Example 2

Synthesis of 10-cycloeicosanone

In a 50 ml four neck reactor equipped with a thermometer and a refrigerant, 10-cycloeicosenone (0.6 g), palladium carbon (0.06 g) and ethanol (10 ml) were introduced. The resulting mixture was heated and stirred for 16 hours at room temperature and under hydrogen atmosphere.

The catalyst was filtered and the solvent was removed under reduced pressure to give 0.6 g of crude product. The crude product was purified on a silica gel column chromatograph (hexane/ethyl acetate=10/1, v/v) to give 0.6 g of 10-cycloeicosanone (quantitative yield).

$^1$H-NMR (500 MHz, CDCl$_3$, d) ppm: 1.20–1.40 (m, 22H), 1.57–1.67 (m, 4H), 1.96–2.04 (m, 4H), 2.37 (t, J=7.3 Hz, 2H), 2.41 (t, J=7.0, 2H) 5.31–5.36 (m, 2H).

IR (film) cm$^{-1}$: 1715.

MS (m/e): 294 (M$^+$) 276, 251, 194, 163, 149, 135, 125, 111, 98, 83, 71, 55, 41, 29.

Synthesis Example 3

Synthesis of Cyclopentadecanol 5.0 g of cyclopentadecanone (MW 224, 22.3 mmol) were dissolved in 5.0 ml of ethanol, and hydrogenated sodium borate (MW 37.8, 2.5 g) was added thereto over 30 minutes. During this period, the temperature of the reaction mixture increased from 20° C. to 50° C. After reaction for one hour at 50° C., 50 ml of hexane and 50 ml of water were successively added, and the reaction was terminated. The reaction mixture was separated into an aqueous phase and an organic phase. The organic phase was washed twice with water and the solvent was removed under reduced pressure to yield a crude product. 4.57 g of crude product were purified on a silica gel column chromatograph (internal diameter 25 mm×height 190 mm, silica gel 60 manufactured by Nakalai Tesque Co. Ltd.) using hexane:ethyl acetate (9:1, v/v), to give 2.35 g of cyclopentadecanol having a purity of 99.3%.

$^1$H-NMR (500 MHz, CDCl$_3$, d) ppm: 1.42–1.28 (m, 24H) 1.47 (m, 2H), 1.57 (m, 2H), 3.57 (m, 1H).

IR (film) cm$^{-1}$: 3280, 1460.

MS (m/e): 208 (M-18), 180, 152, 151, 138, 137, 124, 123, 110, 109, 97, 96, 95, 83, 82, 81, 69, 68, 67, 57, 55, 43, 42, 41.

Synthesis Example 4

Synthesis of 9-cycloheptadecenol

Cyclopentadecanone of Synthesis Example 3 was replaced by civetone, and the ketone group was reduced under the same conditions as in Synthesis Example 3, to give 9-cycloheptadecenol.

$^1$H-NMR (500 MHz, CDCl$_3$, d) ppm: 1.42–1.18 (m, 20H), 1.58–1.42 (m, 4H)., 2.13–2.00 (m, 4H), 3.71 (m, 1H), 5.34 (m, 2H).

IR (film) cm$^{-1}$: 3290, 1460.

MS (m/e): 252(M$^+$), 234(M-18), 149, 135, 121, 109, 96, 95, 94, 93, 83, 82 81, 80, 79, 69, 68, 67, 57, 55, 54, 43, 41.

Synthesis Example 5

Synthesis of 10-cycloeicosenol

In a 500 ml four neck reactor equipped with a thermometer and a refrigerant, methyl 10-undecenoate (25 ml), Grubbs catalyst (0.25 g) and methylene chloride (100 ml) were mixed and stirred for 16 hours at room temperature under nitrogen flow. The solvent was removed from the reaction mixture under reduced pressure. The resulting residue was dissolved in methanol (75 ml) and crystallised at −10° C. over 3 hours. The obtained crystals were filtered and washed with methanol cooled to −10° C. The obtained white crystals were then dried by a vacuum pump to give 7.2 g of 10-eicosendionic acid dimethyl ester.

In a 200 ml four neck reactor equipped with a thermometer, a dripping funnel and a refrigerant, Na (0.9 g) and anhydrous toluene (60 ml) were mixed and stirred at 105° C. under nitrogen flow. 10-eicosendionic acid dimethyl ester (3.7 g) and trimethylsilyl chloride (4.4 g) in anhydrous toluene (60 ml) were added dropwise thereto over 15 minutes. The resulting mixture was refluxed for 2 hours under heating and stirring. The reaction mixture was cooled and quenched into methanol (60 ml). The obtained solution was supplemented with a 5% HCl aqueous solution and ethyl acetate, and allowed to stand to separate into two phases. The obtained organic phase was washed twice with water and washed with a saturated sodium chloride solution. The solvent was then removed under reduced pressure to give 3.4 g of crude product.

The crude product was purified on a silica gel column chromatograph (hexane/ethyl acetate=10/1, v/v) to give 2.4 g of 2-hydroxy-11-cycloeicosenone (yield 77%).

In a 50 ml four neck reactor equipped with a thermometer, a dripping funnel and a refrigerant, zinc powder (2.3 g), 2-hydroxy-11-cycloeicosenone (1.4 g) and toluene (10 ml) were mixed, stirred and heated at 90° C. under a nitrogen flow. A 20N sulphuric acid aqueous solution (2.8 ml) was added thereto dropwise over 2.5 hours, and the resulting mixture was stirred under heating for 30 minutes. After the reaction, the mixture was supplemented with toluene and water, and allowed to stand to separate into two phases. The organic phase thus obtained was washed twice with water and then with a saturated sodium chloride aqueous solution. The solvent was removed under reduced pressure to give 1.4 g of crude product. This latter was purified on a silica gel column chromatography (hexane/ethyl acetate=10/1, v/v) to give 1.2 g of 10-cycloeicosenone (yield 92%).

Cyclopentadecanone of Synthesis Example 3 was replaced by 10-cycloeicosenone, and the ketone group was reduced under the same conditions as in Synthesis Example 3, whereby 10-cycloeicosenol was obtained.

$^1$H-NMR (500 MHz, CDCl$_3$, d) ppm: 1.62–1.18 (m, 28H), 2.06–1.94 (m, 4H) 3.69 (m, 1H), 5.34 (m, 2H).

IR (film) cm$^{-1}$: 3315, 1460.

MS (m/e): 276(M−18), 248, 163, 149, 135, 121, 109, 95, 94, 81, 80, 69, 67, 55, 41, 29.

The compounds of Formula 1, where X is —CO—CHOH— group, can be synthesized e.g. by methods described below.

Measuring Devices and Measuring Conditions:

(5) Gas chromatography (measure of conversion rate)
   Device: HP-5890A (manufactured by Hewlett Packard Co. Ltd)
   Column: Neutrabond-1, 30 m×0.25 mm (GL Science Co. Ltd)
   Carrier gas: helium
   Measuring temperature: 100 to 300° C. (heating rate 10° C./min)

(6) Infrared spectra (1R);
   Device: AVATAR 360 FT-IR (Nicolay Co. Ltd)

(7) Proton nuclear magnetic resonance ($^1$H-NMR)
   Device: DRX-500 (500 MHz) (Bruker Co. Ltd)
   Internal reference substance: tetramethyl silane.

(8) Mass spectra (MS)
   Device: M-80B mass spectrometer (ionisation voltage: 20 eV)
   (Hitachi Seisakusho Co.Ltd)

(9) Melting point: device: MP-S3 type (Yanagimoto Shoji Co. Ltd)

Synthesis Example 6

Synthesis of 2-hydroxy-11-cycloeicosenone (C20)

In a 500 ml four neck reactor equipped with a thermometer and a refrigerant, methyl 10-undecenoate (50 g, 0.252 mol), Grubbs catalyst (0.50 g, 0.566 mol) and methylene chloride (200 ml) were prepared and stirred at room temperature for 16 hours under a nitrogen flow. The solvent of the reaction mixture was then removed under reduced pressure. The residue obtained was dissolved in methanol (150 ml), and crystallised at −10° C. for 3 hours. The crystals obtained were filtered and washed with methanol (150 ml) cooled to −10° C., to obtain white crystals. The latter were dried by a vacuum pump to give 23.0 g of 10-eicosendionic acid dimethyl ester (yield 43.9%).

In a 200 ml four neck reactor equipped with a thermometer, a dripping funnel and a refrigerant, Na (5.74 g, 0.250 mol) and anhydrous toluene (375 ml) were mixed and stirred at 105° C. under nitrogen flow. 10-Eicosendioic acid dimethyl ester (23.0 g, 0.062 mol) and trimethylsilyl chloride (27.1 g, 0.250 mol) in anhydrous toluene (375 ml) were added dropwise thereto over 5 hours. The resulting mixture was refluxed for 2 hours under heating and stirring. The reaction mixture was cooled and quenched into methanol (150 ml). The mixture was then supplemented with a 5% HCl aqueous solution and ethyl acetate, and allowed to stand to separate into two phases. The organic phase thus obtained was washed twice with water and then with a saturated sodium-chloride solution. The solvent was removed under reduced pressure to give 22.8 g of crude product.

The crude product was crystallised in ethanol to give 13.3 g of 2-hydroxy-11-cycloeicosenone (yield 66.6%).

Melting point: 66–67° C.

$^1$H-NMR(500 MHz, CDCl$_3$, δ) ppm:1.14–1.41 (m, 17H), 1.53–1.66 (m, 6H), 1.68–1.80 (m, 1H), 1.83–1.92 (m, 1H), 1.95–2.09 (m, 5H), 2.31–2.40 (m, 1H), 2.5 4–2.62 (m, 1H), 3.52(q, 1H), 4.19–4.23 (m, 1H), 5.30–5.36 (n, 2H).

IR (KBr) cm$^{-1}$: 3425, 1715.

MS (m/e): 308(M$^+$), 292, 278, 265, 249, 235, 223, 207, 193, 180, 163, 149, 135, 121, 111, 98, 81, 67, 55, 41, 29.

Synthesis Example 7

Synthesis of 2-hydroxycycloeicosanone (C20)

In a 50 ml four neck reactor equipped with a thermometer and a refrigerant, 2-hydroxy-11-cycloeicosenone (0.60 g, 1.93 mmol), palladium carbon (0.060 g) and ethanol (10 ml) were mixed. The resulting mixture was heated and stirred for 16 hours at room temperature under hydrogen atmosphere.

The catalyst was filtered and the solvent was removed under reduced pressure to give 0.61 g of crude product. The latter was purified on a silica gel column chromatograph (hexane/ethyl acetate=10/1, v/v) to give 0.60 g of 2-hydroxycycloeicosanone (quantitative yield).

$^1$H-NMR(500MHz, CDCl$_3$, δ) ppm: 1.15–1.44 (m, 28H), 1.44–1.54 (m, 1H), 1.54–1.79 (m, 4H), 1.79–1.90 (m, 1H), 2.32–2.42 (m, 1H), 2.60–2.70 (m, 1H), 3.55 (m, 1H), 4.24 (m, 1H)

IR (NaCl) cm$^{-1}$:3482,1711.

MS (m/e):310 (M$^+$), 292, 279, 267, 249, 236, 223, 211, 193, 179, 165, 151, 137, 123, 109, 96, 82, 69, 55, 41, 29.

Synthesis Example 8

Synthesis of 2-hydroxy-10-cyclooctadecenone (C18)

Methyl-10-undecenoate of Synthesis Example 6 was replaced by methyl 9-decenoate (15.3 g, 0.083 mol), and a metathesis and subsequent treatment were performed to obtain 7.20 g of 9-dimethyloctadecendioate (yield 50.2%) in the same conditions as in Synthesis Example 6. Thereafter, a cyclisation reaction and subsequent treatment gave a crude product. The latter was purified on a silica gel column chromatograph (hexane/ethyl acetate=20/1, v/v), to give 2.40 g of 2-hydroxy-10-cyclooctadecenone (yield 40.5%).

$^1$H-NMR (500 MHz, CDCl$_3$, δ) ppm: 1.19–1.39 (m, 17H), 1.43–1.52 (m, 1H), 1.55–1.65 (m, 1H), 1.67–1.75 (m, 2H), 1.80–1.87 (m, 1H), 2.82–2.33 (m, 1H), 2.50–2.59 (m, 1H), 3.50 (m, 1H), 4.18–4.23 (m, 1H), 5.35–5.37 (m, 2H).

IR (NaCl) cm$^{-1}$: 3480,1710.

MS (m/e):280 (M$^+$), 262, 250, 237, 207, 193, 191, 175, 163, 149, 135, 121, 111, 98, 81, 67, 55, 41, 29.

Synthesis Example 9

Synthesis of 2-hydroxycyclooctadecanone (C18)

2-Hydroxy-11-cycloeicosenone of Synthesis Example 7 was replaced by 2-hydroxy-9-cyclooctadecenone (1.0 g, 3.54 mmol), and a hydrogenation and subsequent treatment were performed under the same conditions as in Synthesis Example 7, to yield 1.0 g of 2-hydroxycyclooctadecanone (quantitative yield).

Melting point: 31–32° C.

$^1$H-NMR (500 MHz, CDCl$_3$, δ) ppm: 1.07–1.38 (m, 24H), 1.38–1.86 (m, 6H), 2.36–2.44 (m, 2H), 2.48–2.57 (m, 1H), 3.48 (m, 1H), 4.19 (m, 1H).

IR (NACl) cm$^{-1}$: 3481, 1712.

MS (m/e):282 (M$^+$), 264, 251, 239, 208, 195, 183, 175, 165, 149, 135, 123, 109, 96, 82, 69, 55, 41, 29

Synthesis Example 10

Synthesis of 2-hydroxy-13-cyclotetracosenone (C24)

Methyl-10-undecenoate of Synthesis Example 6 was replaced by methyl-12-tridecenoate (5.80 g, 0.0256 mol), and a metathesis reaction and subsequent treatment were performed under the same conditions as in Synthesis Example 6, to yield 3.56 g of 12-tetracosendionic acid dimethyl ester (yield 74.6%). Thereafter, a cyclisation reaction and subsequent treatment were performed, to obtain a crude product. The latter was then purified on a silica gel column chromatograph (hexane/ethyl acetate=10/1, v/v) to give 1.88 g of 2-hydroxy-13-cyclotetracosenone (yield 60.9%)

Melting point: 78° C.

$^1$H-NMR (500 MHz, CDCl$_3$, δ) ppm: 1.14–1.40 (m, 26H), 1.48–1.65 (m, 6H), 1.69–1.78 (m, 1H), 1.83–1.90 (m, 1H), 1.94–2.05 (m, 4H), 2.28–2.40 (m, 1H), 2.53–2.61 (m, 1H), 3.56 (m, 1H), 4.20 (m, 1H), 5.31–5.36 (m, 2H).

IR (KBr) cm$^{-1}$: 3489, 1704.

MS (m/e):364 (M$^+$) 346, 334, 321, 281, 265, 252, 237, 223, 207, 191, 177, 163, 149, 135, 121, 109, 95, 81, 67, 55, 41, 29.

Synthesis Example 11

Synthesis of 2-hydroxycyclotetracosanone (C24)

2-Hydroxy-11-cycloeicosenone of Synthesis Example 7 was replaced by 2-hydroxy-13-cyclotetracosenone (0.70 g, 1.92 mmol). The latter was subjected to a hydrogenation reaction and subsequent treatment under the same conditions as in Synthesis Example 7, to give 0.70 g of 2-hydroxycyclotetracosanone (quantitative yield).

Melting point: 39–40° C.

$^1$H-NMR (500 MHz, CDCl$_3$, δ) ppm: 1.21–1.38 (m, 37H), 1.43–1.52 (m, 1H), 1.55–1.64 (m, 2H), 1.66–1.73 (m, 1H), 1.80–1.88 (m, 1H), 2.33–2.41 (m, 1H), 2.50–2.58 (m, 1H), 3.50 (m, 1H), 4.19–4.13 (m, 1H).

IR (KBr) cm$^{-1}$: 3445, 1712.

MS (m/e):366 (M$^+$), 348, 330, 320, 305, 291, 279, 267, 249, 236, 222, 207, 193, 179, 165, 151, 137, 123, 109, 98, 82, 69, 55, 43, 29.

The melanin-synthesis inhibiting effects of the compounds of the present invention are given below, with reference to Examples and Comparative Examples.

Example 1

Inhibiting Effect of the Inventive Compounds on Melanin Synthesis in Pigment Cells In plastic culture flasks (25 cm$^3$), 5×10$^4$ of melanoma cells B-16 were respectively inoculated and cultivated at 37° C. in DMEM culture media each containing 10% of blood serum (Nippon Suisan Co. Ltd) in the presence of 5% of carbon dioxide. After two days of cultivation, test samples diluted with ethanol were added to the culture media, so as to set their concentrations, respectively, at 1.6, 3.1 and 6.3 ppm for the compounds of Formula (1) where X is —CO— or —CHOH—, and at 0.8, 1.6 and 3.1 ppm for the compounds of Formula (1) where X is —CO—CHOH—. The culture media were further cultivated for 4 days.

When the cultivation was terminated, the culture media were removed from the respective flasks and the remaining cells were rinsed with a phosphate buffer solution (PBS hereinafter). The cells in each flask were treated with a culture medium containing trypsin and EDTA (ethylenediaminetetracetic acid) to yield cell suspensions. The latter were subjected to centrifugation, and the cells were recovered.

The obtained cells were once washed with PBS. The residues were observed by eye, and their whiteness was rated as below.

TABLE 1

| Sample | Number of carbon atoms in the ring | 6.3 ppm | 3.1 ppm | 1.6 ppm |
|---|---|---|---|---|
| cyclopentadecanone | 15 | +++ | ++ | + |
| 1-3-methylcyclopentadecanone | 15 | +++ | ++ | + |
| d-3-methylcyclopentadecanone | 15 | +++ | ++ | + |
| cyclohexadecanone | 16 | +++ | ++ | + |
| 5(Z)-cyclohexadecenone | 16 | +++ | ++ | + |
| 5(E)-cyclohexadecenone | 16 | +++ | ++ | + |
| 5(EZ)-4-methylcyclohexadecenone | 16 | +++ | ++ | + |
| 5(E)-4-methylcyclohexadecenone | 16 | +++ | ++ | + |
| cycloheptadecanone | 17 | +++ | ++ | + |
| 9(EZ)-cycloheptadecenone | 17 | +++ | ++ | + |
| cycloeicosanone | 20 | +++ | ++ | + |
| 10(EZ)-cycloeicosenone | 20 | +++ | +++ | ++ |

−: same colour as the comparative solvent example (black)
+: slight colour difference from the comparative solvent example (black grey)
++: clear colour difference from the comparative solvent example (white grey)
+++: no colour in the cells (white)

It is clear from the above results that the macrocyclic ketone derivatives of the invention have a remarkable inhibiting action on melanin synthesis inside pigment cells, compared with any comparative solvent example (control).

This inhibiting activity remarkably depended on the number of carbon atoms in the ring. At a concentration of 3.1 ppm, no activity could be detected when the number of carbon atoms in the ring is less than 12. A sufficiently strong activity could be observed when the ring comprises at least 14 carbon atoms. A particularly strong activity could be observed when the number of carbon atoms in the ring is about 20.

Example 2

Inhibiting Effect of the Inventive Compounds on Melanin Synthesis in Pigment Cells The same operations as mentioned above were performed to detect the inhibiting action on melanin synthesis. The obtained results are shown in Table 2.

TABLE 2

| Sample | Number of carbon atoms in the ring | 6.3 ppm | 3.1 ppm | 1.6 ppm |
|---|---|---|---|---|
| cyclopentadecanol | 15 | +++ | ++ | + |
| cyclohexadecanol | 16 | +++ | ++ | + |
| 5(EZ)-cyclohexadecenol | 16 | +++ | ++ | + |
| 5(EZ)-4-methylcyclohexadecenol | 16 | +++ | ++ | + |
| cycloheptadecanol | 17 | +++ | ++ | + |
| 9(EZ)-cycloheptadecenol | 17 | +++ | ++ | + |
| 10(EZ)-cycloeicosenol | 20 | +++ | +++ | ++ |

It is clear from the above results that the macrocyclic alcohol derivatives of the invention have a remarkable inhibiting action on melanin synthesis inside pigment cells, compared with any comparative solvent example (control).

This inhibiting activity remarkably depended on the number of carbon atoms in the ring. At a concentration of 3.1 ppm, no activity could be detected when the number of carbon atoms in the ring is less than 12. A sufficiently strong activity could be observed when the ring contained at least 14 carbon atoms. A particularly strong activity could be observed when the number of carbon atoms in the ring is about 20.

Comparative Example 1

Using the same method as for Example 1, comparative measures of the melanin synthesis inhibiting action were performed with compounds known for having such inhibiting action and compounds standing outside the scope of the inventive compounds. The results are shown in Table 3.

It is clear from the results shown in Table 3 that the compounds of the present invention have a remarkably strong melanin synthesis inhibiting activity even at low concentrations, compared with arbutin known as a typical melanin synthesis inhibitor, macrocyclic ketoalcohols described in JP-A-Hei 9-151129, and ionols described in JP-A-Hei 8-73334.

TABLE 3

| Comparative compound | Number of carbon atoms in the ring | 6.3 ppm | 3.1 ppm | 1.6 ppm |
| --- | --- | --- | --- | --- |
| 2-hydroxycyclopentadecanone | 15 | +++ | − | − |
| 2-tetradecanone | chain | − | − | |
| 8-pentadecanone | chain | − | − | |
| 3-hexadecanone | chain | − | − | |
| 9-heptadecanone | chain | − | − | |
| dihydro-β-ionone | | ++ | + | − |
| arbutin | | ++ | + | − |
| cyclododecanone | | + | − | |

Comparative Example 2

Using the same method as for Example 1, comparative measures of the melanin synthesis inhibiting action were performed with compounds known for having such inhibiting action and compounds standing outside the scope of the compounds of the present invention. The results are shown in Table 4.

TABLE 4

| Comparative compound | Number of carbon atoms in the ring | 6.3 ppm | 3.1 ppm | 1.6 ppm |
| --- | --- | --- | --- | --- |
| 2-hydroxycyclopentadecanone | 15 | +++ | − | − |
| tetrahydroionol | | ++ | + | − |
| arbutin | | ++ | + | − |
| cyclododecanol | | + | − | |

It is clear from the results shown in Table 4 that the compounds of the present invention have a remarkably strong melanin synthesis inhibiting activity even at low concentration, compared with arbutin known as a typical melanin synthesis inhibitor, macrocyclic ketoalcohols described in JP-A-Hei 9-151129 and ionols described in JP-A-Hei 8-73334.

Example 3

Inhibiting Effect of the Inventive Compounds on Melanin Synthesis in Pigment Cells The same operations as mentioned above were performed to detect the inhibiting action on melanin synthesis. The obtained results are shown in Table 5.

TABLE 5

| sample | Number of carbon atoms in the ring | 3.1 ppm | 1.6 ppm | 0.8 ppm |
| --- | --- | --- | --- | --- |
| 2-hydroxycyclohexadecanone | 16 | + | − | |
| 2-hydroxy-8-cyclohexadecenone | 16 | + | − | |
| 2-hydroxycyclooctadecanone | 18 | +++ | ++ | + |
| 2-hydroxy-9-cyclooctadecenone | 18 | +++ | ++ | + |
| 2-hydroxycycloeicosanone | 20 | +++ | +++ | ++ |
| 2-hydroxy-10-cycloeicosenone | 20 | +++ | +++ | ++ |
| 2-hydroxycyclotetracosanone | 24 | +++ | +++ | ++ |
| 2-hydroxy-12-cyclotetracosenone | 24 | +++ | +++ | ++ |
| 2-hydroxy-15-cyclotriacontenone | 30 | − | | |

It is clear from the above results that the macrocyclic keto-alcohol derivatives of the invention have a remarkable inhibiting action on melanin synthesis inside pigment cells, compared with any comparative solvent example (control).

The inhibiting activity remarkably depended on the number of carbon atoms in the ring. At a concentration of 1.6 ppm, no activity could be detected when the number of carbon atoms in the ring is less than 16. A sufficiently strong activity was observed when the ring contained at least 18 carbon atoms. A particularly strong inhibiting activity was observed when the number of carbon atoms in the ring ranges from more than 20 to 24. On the other hand, when the number of carbon atoms in the ring is 30, the compounds became less soluble, and no particular activity was observed.

Comparative Example 3

Using the same method as in Example 1, the effects of a macrocyclic compound known for its melanin synthesis inhibiting action, and arbutin also known for such activity, were examined under the same conditions as in Example 1. The obtained results are shown in Table 6.

TABLE 6

| Comparative Example | Ring carbons | 3.1 ppm | 1.6 ppm | 0.8 ppm |
| --- | --- | --- | --- | --- |
| 2-hydroxycyclopentadecanone | 15 | − | − | |
| arbutin | | + | − | |

The above results indicate that arbutin and a macrocyclic hydroxyketone (described in JP-A-Hei 9-151129) have much weaker melanin-synthesis inhibiting activities than the compounds of the present invention, even if the latter were applied at lower concentrations.

The following composition examples can also be given to illustrate the external skincare products of the invention.

Composition Example 1

Each of an oil phase and aqueous phase, respectively, containing the ingredients (weight %) described below, was stirred at room temperature to make a homogeneous mixture. The aqueous phase was then added to the oil phase to prepare a cosmetic lotion.

| <oil phase> | |
|---|---|
| 5-cyclohexadecenone | 0.01 |
| ethanol | 20.0 |
| polyoxyethylene hardened castor oil (50E.O.) | 0.05 |
| methyl p-hydroxybenzoate | 0.1 |
| perfume | 0.1 |
| <aqueous phase> | |
| glycerin | 10.0 |
| 1,3-butylene glycol | 5.0 |
| purified water | remaining part |

The obtained cosmetic lotion has an excellent whitening effect and a good storage stability compared to preparations which do not contain the compounds of the invention.

Composition Example 2

Each of an oil phase and aqueous phase, respectively, containing the ingredients (weight %) described below, was stirred at room temperature to make a homogeneous mixture. The aqueous phase was then added to the oil phase to prepare a milky emulsion.

| <oil phase> | |
|---|---|
| cycloheptadecanone | 0.1 |
| stearic acid | 2.0 |
| liquid paraffin | 6.0 |
| squalene | 2.0 |
| sorbitan monostearate | 1.5 |
| polyoxyethylenesorbitan monostearate (20E.O.) | 2.0 |
| butyl p-hydroxybenzoate | 0.05 |
| methyl p-hydroxybenzoate | 0.1 |
| perfume | 0.15 |
| <aqueous phase> | |
| glycerin | 5.0 |
| 1,3-butylene glycol | 5.0 |
| purified water | remaining part |

The obtained milky emulsion has an excellent whitening effect and a good storage stability compared with preparations which do not contain the compounds of the invention.

Composition Example 3

The ingredients (weight %) of each of the oil phase and aqueous phase below were mixed at 70° C. and dissolved. The oil phase was added slowly to the aqueous phase to make a pre-emulsion. The latter was further mixed by a "homomixer" to give an emulsion. The latter was cooled to 30° C. under strong stirring, to give a cream.

| <oil phase> | |
|---|---|
| 10(E)-cycloeicosenone | 0.1 |
| stearic acid | 2.0 |
| liquid paraffin | 23.0 |
| vaseline | 7.0 |
| sorbitan monostearate | 3.5 |
| beeswax | 2.0 |

| -continued | |
|---|---|
| behenyl alcohol | 1.0 |
| polyoxyethylenesorbitan monostearate (20E.O.) | 2.5 |
| butyl p-hydroxybenzoate | 0.05 |
| methyl p-hydroxybenzoate | 0.1 |
| perfume | 0.15 |
| <aqueous phase> | |
| glycerin | 5.0 |
| 1,3-butylene glycol | 5.0 |
| purified water | remaining part |

The obtained cream has an excellent whitening effect and a good storage stability compared with preparations which do not contain the compounds of the invention.

Composition Example 4

Each of an oil phase and aqueous phase, respectively, containing the ingredients (weight %) described below, was stirred at room temperature to make a homogeneous mixture. The aqueous phase was then added to the oil phase to prepare a cosmetic lotion.

| <oil phase> | |
|---|---|
| 5-cyclohexadecenol | 0.01 |
| ethanol | 20.0 |
| polyoxyethylene hardened castor oil (50E.O.) | 0.05 |
| methyl p-hydroxybenzoate | 0.1 |
| perfume | 0.1 |
| <aqueous phase> | |
| glycerin | 10.0 |
| 1,3-butylene glycol | 5.0 |
| purified water | remaining part |

The obtained cosmetic lotion has an excellent whitening effect and a good storage stability compared with preparations which do not contain the compounds of the invention.

Composition Example 5

Each of an oil phase and aqueous phase, respectively containing the ingredients (weight %) described below, was stirred at room temperature to make a homogeneous mixture. The aqueous phase was then added to the oil phase to prepare a cosmetic lotion.

| <oil phase> | |
|---|---|
| cycloheptadecanol | 0.1 |
| stearic acid | 2.0 |
| liquid paraffin | 6.0 |
| squalene | 2.0 |
| sorbitan monostearate | 1.5 |
| polyoxyethylenesorbitan monostearate (20E.O.) | 2.0 |
| butyl p-hydroxybenzoate | 0.05 |
| methyl p-hydroxybenzoate | 0.1 |
| perfume | 0.15 |
| <aqueous phase> | |
| glycerin | 5.0 |
| 1,3-butylene glycol | 5.0 |
| purified water | remaining part |

The obtained cosmetic emulsion has an excellent whitening effect and a good storage stability compared with preparations which do not contain the compounds of the invention.

Composition Example 6

The ingredients (weight %) of each of the oil phase and aqueous phase below were mixed at 70° C. and dissolved.

The oil phase was added slowly to the aqueous phase to make a pre-emulsion. The latter was further mixed by a "homomixer" to give an emulsion. The latter was cooled to 30° C. under strong stirring, to give a cream.

| <oil phase> | |
|---|---|
| cycloeicosenol | 0.1 |
| stearic acid | 2.0 |
| liquid paraffin | 23.0 |
| vaseline | 7.0 |
| sorbitan monostearate | 3.5 |
| beeswax | 2.0 |
| behenyl alcohol | 1.0 |
| polyoxyethylenesorbitane monostearate (20E.O.) | 2.5 |
| butyl p-hydroxybenzoate | 0.05 |
| methyl p-hydroxybenzoate | 0.1 |
| perfume | 0.15 |
| <aqueous phase> | |
| glycerine | 5.0 |
| 1,3-butylene glycol | 5.0 |
| purified water | remaining part |

The obtained cream has an excellent whitening effect and a good storage stability compared with preparations which do not contain the compounds of the invention.

Composition Example 7

Each of an oil phase and aqueous phase, respectively, containing the ingredients (weight %) described below, was stirred at room temperature to make a homogeneous mixture. The aqueous phase was then added to the oil phase to prepare a cosmetic lotion.

| <oil phase> | |
|---|---|
| 2-hydroxy-10-cycloeicosenone | 0.01 |
| ethanol | 20.0 |
| polyoxyethylene solidified castor oil (50E.O.) | 0.05 |
| methyl p-hydroxybenzoate | 0.1 |
| perfume | 0.1 |
| <aqueous phase> | |
| glycerin | 10.0 |
| 1,3-butylene glycol | 5.0 |
| purified water | remaining part |

The obtained cosmetic lotion has an excellent whitening effect and a good storage stability, compared with preparations which do not contain the compounds of the invention.

Composition Example 8

The ingredients (weight %) of each of the oil phase and aqueous phase below were mixed at 70° C. and dissolved. The aqueous phase was added to the oil phase to make a milky emulsion.

| <oil phase> | |
|---|---|
| 2-hydroxycyclooctadecanone | 0.1 |
| stearic acid | 2.0 |
| liquid paraffin | 6.0 |
| squalene | 2.0 |
| sorbitan monostearate | 1.5 |
| polyoxyethylensorbitan monostearate (20E.O.) | 2.0 |
| butyl p-hydroxybenzoate | 0.05 |
| methyl p-hydroxybenzoate | 0.1 |
| perfume | 0.15 |
| <aqueous phase> | |
| glycerin | 5.0 |
| 1,3-butylene glycol | 5.0 |
| purified water | remaining part |

The obtained emulsion has an excellent whitening effect and a good storage stability compared with preparations which do not contain the compounds of the invention.

Composition Example 9

The ingredients (weight %) of each of the oil phase and aqueous phase below were mixed at 70° C. and dissolved. The oil phase was added slowly to the aqueous phase to make a pre-emulsion. The latter was further mixed by a "homomixer" to give an emulsion. The latter was cooled to 30° C. under strong stirring, to give a cream.

| <oil phase> | |
|---|---|
| 2-hydroxy-12-cyclotetracosenone | 0.1 |
| stearic acid | 2.0 |
| liquid paraffin | 23.0 |
| vaseline | 7.0 |
| sorbitan monostearate | 3.5 |
| beeswax | 2.0 |
| behenyl alcohol | 1.0 |
| polyoxyethylenesorbitan monostearate (20E.O.) | 2.5 |
| butyl p-hydroxybenzoate | 0.05 |
| methyl p-hydroxybenzoate | 0.1 |
| perfume | 0.15 |
| <aqueous phase> | |
| glycerin | 5.0 |
| 1,3-butylene glycol | 5.0 |
| purified water | remaining part |

The obtained cream has an excellent whitening effect and a good storage stability, compared with preparations which do not contain the compounds of the invention.

Composition Example 10

Component A below was dispersed and dissolved at room temperature. Component B below was added thereto, and the mixture was homogeneously dissolved to prepare a pack. The compositions of components A and B are expressed below in weight %.

| <A component> | |
|---|---|
| polyvinyl alcohol | 15.0 |
| purified water | 40.0 |
| <B component> | |
| ethanol | 4.0 |
| 1,3-butylene glycol | 4.0 |
| polyoxyethylene(8)polyoxypropylene glycol (55) | 3.0 |
| bisabolol | 0.5 |
| tocopherol | 0.02 |

-continued

| | |
|---|---|
| 2-hydroxycycloeicosenone | 0.5 |
| Parsol ® 1789* (Givaudan Co. Ltd) (ultraviolet ray absorbent) | 2.0 |
| purified water | remaining part |

(*Parsol ® 1789: 4-methoxybenzoyl-4'-t-butylbenzoylmethane)

The obtained pack agent has an excellent whitening effect and a good storage stability, compared with preparations which do not contain the compounds of the invention.

Composition Example 11

Each of an oil phase and aqueous phase, respectively, containing the ingredients (weight %) described below, was stirred at room temperature to make a homogeneous mixture. The aqueous phase was then added to the oil phase to prepare a cosmetic lotion.

| <oil phase> | |
|---|---|
| 2-hydroxy-9-cyclooctadecenone | 0.05 |
| ethanol | 20.0 |
| polyoxyethylene hardened castor oil (50E.0.) | 0.05 |
| methyl p-hydroxybenzoate | 0.1 |
| perfume | 0.1 |
| Parsol ® 1789 (Givaudan Co. Ltd) (ultraviolet ray absorbent) | 2.0 |
| <aqueous phase> | |
| glycerin | 10.0 |
| 1,3-butylene glycol | 5.0 |
| purified water | remaining part |

(*Parsol ® 1789: 4-methoxybenzoyl-4'-t-butylbenzoylmethane)

The obtained cosmetic lotion has an excellent whitening effect and a good storage stability, compared with preparations which do not contain the compounds of the invention.

The present invention provides new melanin-synthesis inhibitor compositions, which are very stable and safe, and exhibit a high melanin synthesis inhibition effect. Moreover, when prepared as an external skincare product containing such compositions, the product is also very stable and safe in a base preparation as well as in a prescribed form, and shows a remarkable whitening effect.

Although the invention has been described with reference to particular means, materials and embodiments, it is to be understood that the invention is not limited to the particulars disclosed and extends to all equivalents within the scope of the claims.

The present disclosure relates to subject-matter contained in priority Japanese Applications Nos. 2001-173655 and 2001-315378, respectively, filed on June 8 and Oct. 12, 2001, which are both herein expressly incorporated by reference in their entireties.

What is claimed:

1. A melanin-synthesis inhibitor composition containing at least one macrocyclic compound represented by Formula (1)

wherein X signifies a member selected among the group consisting of —C—, —CHOH— and —CO—CHOH—; R signifies a chain hydrocarbon having 13 to 24 carbon atoms and forming a ring with X; and R either is saturated or contains 1 to 3 unsaturated bonds, and may be substituted with a lower alkyl group of 1 to 3 carbon atoms, with the proviso that, when X is —CO—CHOH—, the number of carbon atoms in said chain hydrocarbon is not 13; and, optionally, a skin whitening agent and/or ultra-violet ray absorbent.

2. A melanin-synthesis inhibitor composition according to claim 1, wherein X signifies a —CO— group.

3. A melanin-synthesis inhibitor composition according to claim 2, containing at least one compound selected from the group consisting of cyclotetradecanone, cyclopentadecanone, cyclohexadecanone, cycloheptadecanone, cyclooctadecanone, cyclononadecanone, cycloeicosanone, cycloheneicosanone, cyclodocosanone, cyclotricosanone, cyclotetracosanone, cyclopentacosanone, 3-methylcyclopentadecanone, (S)-3-methylcyclopentadecanone, (R)-3-methylcyclopentadecanone, 3-methylcyclohexadecanone, 4-methylcyclohexadecanone, 4-cyclopentadecenone, 5-cyclopentadecenone, 4-cyclohexadecenone, 5-cyclohexadecenone, (E)-5-cyclohexadeceflone, (Z)-5-cyclohexadecenone, 9-cyclopentadecenone, (E)-9-cyclopentadecenone, (Z)-9-cyclopentadecenone, 3-methyl-4-cyclopentadecenone, 3-methyl-5-cyclopentadecenone, 3-methyl-4-cyclohexadecenone, 3-methyl-5-cyclohexadecenone, 4-methyl-4-cyclohexadecenone, 4-methyl-5-cyclohexadecenone, 10-cycloeicosenone, 11-cyclodocosenone and 12-cyclotetracosenone.

4. A melanin-synthesis inhibitor composition according to claim 1, wherein X signifies a —CHOH— group.

5. A melanin-synthesis inhibitor composition according to claim 4, containing at least one compound selected from the group consisting of cyclotetradecanol, cyclopentadecanol, cyclohexadecanol, cycloheptadecanol, cyclooctadecanol, cyclononadecanol, cycloeicosanol, cycloheneicosanol, cyclodocosanol, cyclotricosanol, cyclotetracosanol, cyclopentacosanol, 3-methylcyclopentadecanol, (1R,3R)-3-methylcyclopentadecanol, (1R,3S)-3-methylcyclopentadecanol, (1S, 3R)-3-methylcyclopentadecanol, (1S,3S)-3-methylcyclopentadecanol, 3-methylcyclohexadecanol, 4-methylcyclohexadecanol, 4-cyclopentadecenol, 5-cyclopentadecenol, 4-cyclohexadecenol, 5-cyclohexadecenol, (E)-5-cyclohexadecenol, (S)-5-cyclohexadecenol, 9-cycloheptadecenol, (E)-9-cycloheptadecenol, (S)-9-cycloheptadecenol, 3-methyl-4-cyclopentadecenol, 3-methyl-5cyclohexadecenol, 4-methyl-4-cyclohexadecenol, 4-methyl-5-cyclohexadecenol, 10-cycloeicosenol, 11-cyclodocosenol and 12-cyclotetracosenol.

6. A melanin synthesis inhibitor composition according to claim 1, containing at least one macrocyclic compound of Formula (1) where X signifies group —CO—, and at least one macrocyclic compound of Formula (1) where X signifies group —CHOH—.

7. A melanin synthesis inhibitor composition according to claim 1, wherein X signifies a —CO—CHOH— group, R being a chain hydrocarbon having 14 to 24 carbon atoms.

8. A melanin synthesis inhibitor composition according to claim 7, containing at least one compound selected from the group consisting of 2-hydroxycyclohexadecanone, 2-hydroxycycloheptadecanone, 2-hydroxycyclooctadecanone, 2-hydroxycyclononadecanone, 2-hydroxycycloeicosanone, 2-hydroxycycloheneicosanone, 2-hydroxycyclodocosanone, 2-hydroxycyclotricosanone, 2-hydroxycyclotetracosanone, 2-hydroxycycloheptacosanone, 2-hydroxycyclohexacosanone, 2-hydroxycyclo-3methycycloeicosanone 2-hydroxy-20-methylcycloeicosanone, 2-hydroxy-4, 19-dimethylcycloeicosanone, (4R)-2-hydroxy4-methylcycloeicosanone, (19R)-2-hydroxy-19-methylcycloeicosanone, 2-hydroxy-8-cyclohexadecenone, 2-hydroxy-9-cycloheptadecenone, 2-hydroxy-10-cyclooctadecenone, 2-hydroxy-10-cyclononadecenone, 2-hydroxy-11-cycloeicosenone, (Z)-2-hydroxy-11-cycloeicosenone, (E)-2-hydroxy-11-cycloeicosenone, 2-hydroxy-10-cycloheneicosenone, 2-hydroxy-11-cyclodocosenone, 2-hydroxy-13-cyclotetracosenone, 2-hydroxy-3-methyl-11-cycloeicosenone, 2-hydroxy-20-methyl-1-cycloeicosenone, 2-hydroxy-4,19-dimethyl-11-cycloeicosenone, (4S)-2-hydroxy-4-methyl-11-cycloeicosenone, (19S)-2-hydroxy-19-methyl-11-cycloeicosenone, (5E, 15E)-2-hydroxy5, 15-cyclooctadecadienone, (5E, 17E)-2-hydroxy-4, 19-dimethyl-5, 17-cycloeicosadienone.

9. A melanin synthesis inhibitor composition according to claim 7, wherein X signifies a —CO—CHOH— group, R being a chain hydrocarbon having 16 to 22 carbon atoms.

10. A melanin synthesis inhibitor composition according to claim 8, wherein X signifies a —CO—CHOH— group, R being a chain hydrocarbon having 18 or 19 carbon atoms.

11. A melanin synthesis inhibitor composition according to claim 10, containing at least one compound selected from the group consisting of 2-hydroxycycloeicosanone, 2-hydroxycycloheneicosanone, 2-hydroxy-11-cycloeicosenone, 2-hydroxy-11-cycloheneicosenone and 2-hydroxy-12-cycloheneicosenone.

12. An external skincare product containing a melanin-synthesis inhibitor composition comprising at least one macrocyclic compound represented by Formula (1)

(1)

wherein X signifies a group selected among the groups consisting of —CO—, —CHOH— and —CO—CHOH—; R signifies a chain hydrocarbon having 13 to 24 carbon atoms and forming a ring with X; and R either is saturated or contains 1 to 3 unsaturated bonds, and may be substituted with a lower alkyl group of 1 to 3 carbon atoms, with the proviso that, when X is —CO—CHOR—, the number of carbon atoms in said chain hydrocarbon is not 13;
and a cosmetically and/or dermatologically acceptable medium.

13. An external skincare product according to claim 12, wherein said at least one melanin-synthesis inhibitor composition is contained in a concentration ranging from 0.00001 to 10 weight %.

14. A macrocyclic compound represented by Formula (1'):

(1')

wherein X signifies a —CO—CHOH— group; R signifies a chain hydrocarbon having 18 or 19 carbon atoms and forming a ring with X; and R either is saturated or contains 1 to 3 unsaturated bonds, and may be substituted with a lower alkyl group of 1 to 3 carbon atoms.

15. A macrocyclic compound according to claim 14, selected from the group consisting of 2-hydroxycloeicosanone, 2hydroxycycloheneicosanone, 2-hydroxy-11-cycloeicosenone, 2-hydroxy-11-cycloheneicosenone and 2-hydroxy-12-cycloheneicosenone.

16. A method of preparing a macrocyclic compound according to claim 14, characterized in that said method comprises the steps of:

preparing a corresponding unsaturated chain hydrocarbon having 20 or 21 carbon atoms, whose both end carbons form esterified carboxy groups;

subjecting said esters to an acyloin condensation, so that an unsaturated macrocyclic compound is obtained; and optionally, subjecting said unsaturated macrocyclic compound to subsequent hydrogenation.

17. A process of inhibiting melanin synthesis comprising applying to skin requiring such melanin inhibition a melanin-synthesis inhibitor composition containing at least one macrocyclic compound represented by Formula (1)

(1)

wherein X signifies a group selected among the groups consisting of —CO—, —CHOH— and —CO—CHOH—; R signifies a chain hydrocarbon having 13 to 24 carbon atoms and forming a ring with X; and R either is saturated or contains 1 to 3 unsaturated bonds, and may be substituted with a lower alkyl group of 1 to 3 carbon atoms, with the proviso that, when X is —CO—CHOH—, the number of carbon atoms in said chain hydrocarbon is not 13.

* * * * *

UNITED STATES PATENT AND TRADEMARK OFFICE
CERTIFICATE OF CORRECTION

PATENT NO. : 6,759,557 B2
DATED : July 6, 2004
INVENTOR(S) : Hiroyuki Matsuda et al.

It is certified that error appears in the above-identified patent and that said Letters Patent is hereby corrected as shown below:

<u>Title page,</u>
Item [56], References Cited, FOREIGN PATENT DOCUMENTS, insert
-- JP 2002-145718 A 05/2002 --.

Signed and Sealed this

Twenty-sixth Day of April, 2005

JON W. DUDAS
*Director of the United States Patent and Trademark Office*